US008728517B2

United States Patent
Kapoor et al.

(10) Patent No.: US 8,728,517 B2
(45) Date of Patent: *May 20, 2014

(54) PHARMACEUTICAL COMPOSITIONS OF ENTACAPONE CO-MICRONIZED WITH SUGAR ALCOHOLS

(75) Inventors: Ritesh Kapoor, Ahmedabad (IN); Sanjay Mate, Aurangabad (IN); Munish Talwar, Aurangabad (IN); Girish Kumar Jain, Aurangabad (IN)

(73) Assignee: Wockhardt Ltd., Bandra East, Mumbai (IN)

( * ) Notice: Subject to any disclaimer, the term of this patent is extended or adjusted under 35 U.S.C. 154(b) by 124 days.

This patent is subject to a terminal disclaimer.

(21) Appl. No.: 12/865,783

(22) PCT Filed: Feb. 6, 2009

(86) PCT No.: PCT/IB2009/050490
§ 371 (c)(1),
(2), (4) Date: Nov. 22, 2010

(87) PCT Pub. No.: WO2009/098663
PCT Pub. Date: Aug. 13, 2009

(65) Prior Publication Data
US 2011/0052681 A1    Mar. 3, 2011

(30) Foreign Application Priority Data
Feb. 6, 2008    (IN) .......................... 264/MUM/2008

(51) Int. Cl.
*A61K 9/48*    (2006.01)
*A61K 31/277*    (2006.01)
*A61K 9/14*    (2006.01)
*A61P 25/16*    (2006.01)

(52) U.S. Cl.
USPC ........................... 424/451; 514/521; 424/489

(58) Field of Classification Search
None
See application file for complete search history.

(56) References Cited

U.S. PATENT DOCUMENTS 6,797,732 B2 *    9/2004    Virkki et al. .................. 514/646
2008/0187590 A1 *    8/2008    Vahervuo ..................... 424/474

FOREIGN PATENT DOCUMENTS

| GB | 2429645 A | | 3/2007 | |
| WO | WO0015196 A1 | | 3/2000 | |
| WO | WO 01/01984 | * | 6/2000 | ........... A61K 31/198 |
| WO | WO 01/01984 | * | 11/2001 | |
| WO | WO 2006/131591 | * | 12/2006 | ........... A61K 31/275 |
| WO | WO2006131591 A2 | | 12/2006 | |

OTHER PUBLICATIONS http://medical-dictionary.thefreedictionary.com/micronization.*

* cited by examiner

*Primary Examiner* — Robert A Wax
*Assistant Examiner* — Danah Al-Awadi
(74) *Attorney, Agent, or Firm* — Bio Intellectual Property Services LLC (Bio IPS); O. (Sam) Zaghmout

(57) ABSTRACT

The present invention relates to pharmaceutical compositions comprising entacapone or pharmaceutically acceptable salts thereof along with one or more sugar alcohols; wherein the entacapone is co-micronized with one or more sugar alcohols. The invention also relates to processes of making such compositions.

14 Claims, No Drawings

PHARMACEUTICAL COMPOSITIONS OF ENTACAPONE CO-MICRONIZED WITH SUGAR ALCOHOLS

FIELD OF THE INVENTION

The present invention relates to pharmaceutical compositions comprising entacapone or pharmaceutically acceptable salts thereof along with one or more sugar alcohols, wherein the entacapone is co-micronized with one or more sugar alcohols. The invention also relates to processes for making such compositions.

BACKGROUND OF THE INVENTION

Entacapone, an inhibitor of catechol-O-methyltransferase (COMT), is a nitro-catechol-structured compound used in the treatment of Parkinson's disease as an adjunct to levodopa/carbidopa therapy. Chemically, entacapone is (E)-2-cyano-3-(3,4-dihydroxy-5-nitrophenyl)-N,N-diethyl-2-propenamide having the following structural formula:

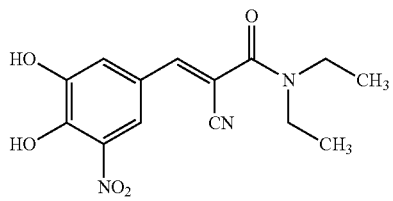

Entacapone is a class IV drug under the Biopharmaceutics Classification system and poses problems of low solubility, low dissolution rate and hence low bioavailability.

U.S. Pat. No. 4,963,590 provides a pharmaceutical composition comprising entacapone and pharmaceutically acceptable carrier.

U.S. Pat. No. 6,599,530 provides an oral compacted composition in the form of a tablet which includes entacapone, nitecapone, or pharmaceutically acceptable salt of entacapone or nitecapone, and croscarmellose sodium in an amount of at least 6% by weight of the composition.

International Publication No. WO2006/131591 discloses oral dosage forms of entacapone and methods of preparation thereof.

Although it is known that micronization or grinding of a substance in the presence of a surfactant or sugar can increase its solubility, these parameters are not always adequate. For example, the bioavailability of micronized progesterone is not adequate and should be improved, for example by dispersion in carnauba wax. Such a technique is described in International Publication No. (PCT) WO 8902742. Thus, it appears that the properties of a substance treated by micronization or grinding, in particular its solubility and its bioavailability, are not predictable and contradictory results may be obtained.

There are numerous prior art references which disclose the use of sugar alcohols like mannitol, sorbitol etc. as fillers in the formulation or as sensory cue agents, i.e. the agents which impart feeling of cooling in mouth in case of orally disintegrating tablets. For example, International Publication Nos. (PCT) WO 2007080601, 2007001086, 2006057912; European Patent Nos. 589981 B1, 906089B1, 1109534B1; U.S. Pat. No. 6,328,994, and US Application Nos. 20070196494, 20060240101, and 20060057199. Sugar alcohols like mannitol are employed in the most orally disintegrating formulations and not in the conventional immediate release formulations as sensory cue agents because the orally disintegrating tablets disintegrate in mouth instead of disintegrating in the gastrointestinal tract as in the case of conventional immediate release tablets.

SUMMARY OF THE INVENTION

In one general aspect there is provided a single oral dose pharmaceutical composition comprising entacapone or salts thereof along with one or more sugar alcohols, wherein the entacapone is co-micronized with one or more sugar alcohols.

Embodiments of the pharmaceutical composition may include one or more of the following features. For example, the pharmaceutical composition may further include one or more pharmaceutically acceptable excipients. The pharmaceutically acceptable excipients may include one or more binders, fillers, lubricants, disintegrants, glidants, and the like.

In another general aspect there is provided a pharmaceutical composition comprising entacapone or salts thereof along with one or more sugar alcohols; wherein the entacapone is co-micronized with one or more sugar alcohols; wherein the composition exhibits a dissolution profile such that at least 80% of entacapone or salt thereof is released within 30 minutes; and wherein the release rate is measured in USP Dissolution Apparatus 2 (paddle, 50 rpm) using 1000 ml of pH 5.5 phosphate buffer at 37° C.±0.5° C.

Embodiments of the pharmaceutical composition may include one or more of the following features. For example, the pharmaceutical composition may further include one or more pharmaceutically acceptable excipients. The pharmaceutically acceptable excipients may include one or more binders, fillers, lubricants, disintegrants, glidants, and the like.

In yet another aspect there is provided a process for preparing a pharmaceutical composition. The process includes co-micronizing entacapone or salts thereof with one or more sugar alcohols, mixing with other pharmaceutically acceptable excipients, and forming the mixture into a pharmaceutical dosage form.

Embodiments of the pharmaceutical composition may include one or more of the following features. For example, the pharmaceutically acceptable excipients may include one or more binders, fillers, lubricants, disintegrants, glidants and the like.

The pharmaceutical composition of the present invention can be present in the form of a tablet, a capsule, powder, a disc, a caplet, granules, pellets, granules in a capsule, minitablets, minitablets in a capsule, pellets in a capsule, a sachet and other dosage forms suitable for oral administration.

The details of one or more embodiments of the inventions are set forth in the description below. Other features, objects and advantages of the inventions will be apparent from the description and claims.

DETAILED DESCRIPTION OF THE INVENTION

The inventors have noticed that sugar alcohols like mannitol or sorbitol when used along with other known water insoluble drugs like fenofibrate, irbesartan, aripiprazole, either as a physical mixture or in the form of a complex, it does not make any significant difference either in solubility or percent release of these poorly soluble drugs.

The inventors while working on the entacapone formulation have surprisingly found that when entacapone is co-micronized with sugar alcohols; it results in a significant increase in the solubility of entacapone and percent drug release of entacapone vis-à-vis the formulation wherein the entacapone is not co-micronized with a sugar alcohol.

Comtan® releases about 70% of entacapone in 20 minutes, whereas the pharmaceutical composition of the present invention releases almost 100% of the entacapone in 20 minutes. This significant increase in percent release of entacapone leads to improved wettability, solubility, and hence increased percent release.

Suitable sugar alcohols may include one or more of mannitol, maltitol, maltol, sorbitol, lactitol, xylitol, and the like.

In the pharmaceutical composition of the invention, the entacapone can be present in an amount relative to the sugar alcohol, such that a molar ratio between the entacapone and the sugar alcohol is from about 1:1 to 10:1.

The co-micronization can be carried out by suitable means known in the art, which include but not limited to one or more of nano mill, ball mill, attritor mill, vibratory mill, sand mill, bead mill, jet mill, ultrasonication, and the like.

The mean particle size of entacapone and sugar alcohol obtained after co-micronization may be less than 30μ.

The pharmaceutical composition can be prepared by co-micronizing entacapone with one or more suitable sugar alcohols, mixing, and granulating with other pharmaceutically acceptable excipients. The granules may be mixed with other suitable pharmaceutically acceptable excipients.

The pharmaceutical composition of the present invention can be present in the form of a tablet, a capsule, powder, a disc, a caplet, granules, pellets, granules in a capsule, minitablets, minitablets in a capsule, pellets in a capsule, a sachet and other dosage forms suitable for oral administration.

The pharmaceutical composition may further include one or more pharmaceutically acceptable excipients. The pharmaceutically acceptable excipients may include one or more of binders, fillers, lubricants, disintegrants, and glidants.

Suitable binders may include one or more of povidone, starch, stearic acid, gums, hydroxypropylmethylcellulose, and the like.

Suitable fillers may include one or more of microcrystalline cellulose, lactose, mannitol, calcium phosphate, calcium sulfate, kaolin, dry starch, powdered sugar, and the like.

Suitable lubricants may include one or more of magnesium stearate, zinc stearate, calcium stearate, stearic acid, sodium stearyl fumarate, hydrogenated vegetable oil, and the like.

Suitable glidants may include one or more of colloidal silicon dioxide, talc or cornstarch, and the like.

Suitable disintegrants may include one or more of starch, croscarmellose sodium, crosspovidone, sodium starch glycolate, and the like.

The invention is further illustrated by the following examples which are provided merely to be exemplary of the invention and do not limit the scope of the invention. Certain modifications and equivalents will be apparent to those skilled in the art and are intended to be included within the scope of the present invention.

Example 1

The composition of batches is provided in table 1. Following formulations are representatives of the preferred compositions of the present invention. The preparation of example 1 is detailed below.

TABLE 1

Composition of entacapone

| No | Ingredients | % Composition |
|---|---|---|
| | Entacapone Granules | |
| 1 | Entacapone | 15-65 |
| 2 | Mannitol | 5-50 |
| 3 | Polyvinyl pyrrolidone | 0.5-8 |
| 4 | Crospovidone | 2-10 |
| 5 | Magnesium stearate | 0.2-3 |

Procedure: Entacapone and mannitol were mixed and co-micronized through a multimill. To the co-micronized mixture, crospovidone, povidone and magnesium stearate were added, mixed and granulated using a roll compactor to obtain granules of a suitable size. Crospovidone and magnesium stearate were added to the granules and the resultant mixture was compressed into tablets using a suitable tooling.

TABLE 2

Comparative dissolution data of Comtan ® vs composition of the present invention prepared as per example 1. For determination of drug release rate, USP Type 2 Apparatus (rpm 50) was used wherein 900 ml of pH 5.5 phosphate buffer at 37° C. ± 0.5° C. was used as medium.

| Time (min) | % drug released (Comtan ®) | % drug released (Example-1) |
|---|---|---|
| 10 | 35 | 93 |
| 20 | 70 | 100 |
| 30 | 78 | 100 |
| 45 | 91 | 100 |

While the invention has been described in terms of its specific embodiments, certain modifications and equivalents will be apparent to those skilled in the art and are intended to be included within the scope of the invention.

We claim:

1. A pharmaceutical composition comprising entacapone or salts thereof along with one or more sugar alcohols; wherein the entacapone is co-micronized with one or more sugar alcohols, wherein the co-micronized entacapone and sugar alcohol mixture so obtained has a mean particle size of less than about 30μ.

2. The pharmaceutical composition of claim 1, wherein the entacapone and sugar alcohol are present in a molar ratio from about 1:1 to 10:1.

3. The pharmaceutical composition of claim 1, wherein the sugar alcohols comprise one or more of mannitol, maltitol, maltol, sorbitol, lactitol and xylitol.

4. The pharmaceutical composition of claim 1, wherein the composition comprises one or more of a tablet, a capsule, powder, a disc, a caplet, granules, pellets, granules in a capsule, minitablets, minitablets in a capsule, pellets in a capsule and a sachet.

5. The pharmaceutical composition of claim 1 further comprises one or more pharmaceutically acceptable excipients.

6. The pharmaceutical composition of claim 5, wherein the pharmaceutical acceptable excipients comprise one or more of binders, fillers, lubricants, disintegrants, and glidants.

7. The pharmaceutical composition of claim 1, wherein the composition exhibits a dissolution profile such that at least 80% of the entacapone is released within 30 minutes; and wherein the release rate is measured in Apparatus 2 (USP, Dissolution, paddle, 50 rpm) using 1000 ml of pH 5.5 phosphate buffer at 37° C.±0.5° C.

8. The pharmaceutical composition of claim 7 further comprises one or more pharmaceutically acceptable excipients.

9. The pharmaceutical composition of claim 8, wherein the pharmaceutical acceptable excipients comprise one or more of binders, fillers, lubricants, disintegrants, and glidants.

10. A process for preparing a pharmaceutical composition of claim 1, the process comprising co-micronizing entacapone or salts thereof with one or more sugar alcohols, mixing with other pharmaceutically acceptable excipients and forming the mixture into a pharmaceutical dosage form.

11. The process of claim 10, wherein the sugar alcohols comprise one or more of mannitol, maltitol, maltol, sorbitol, lactitol and xylitol.

12. The process of claim 10, wherein the pharmaceutical acceptable excipients comprise one or more of binders, fillers, lubricants, disintegrants, and glidants.

13. The process of claim 10, wherein the co-micronization is carried out by one or more of nano mill, ball mill, attritor mill, vibratory mill, sand mill, bead mill, jet mill and ultrasonication.

14. The process of claim 10, wherein the pharmaceutical dosage form comprises one or more of a tablet, a capsule, powder, a disc, a caplet, granules, pellets, granules in a capsule, minitablets, minitablets, in a capsule, pellets in a capsule and a sachet.

* * * * *